United States Patent [19]
Asano et al.

[11] Patent Number: 5,703,959
[45] Date of Patent: Dec. 30, 1997

[54] METHOD AND DEVICE FOR ANALYZING PARTICLES

[75] Inventors: Kaoru Asano, Kobe; Kimiyo Kubo, Kakogawa, both of Japan

[73] Assignee: Toa Medical Electronics Co., Ltd., Kobe, Japan

[21] Appl. No.: 368,053

[22] Filed: Jan. 3, 1995

Related U.S. Application Data

[63] Continuation of Ser. No. 76,870, Jun. 15, 1993, abandoned.

[30] Foreign Application Priority Data

Jun. 19, 1992 [JP] Japan .................. 4-186265

[51] Int. Cl.$^6$ .................. G06K 9/62
[52] U.S. Cl. .................. 382/133; 364/555; 382/225
[58] Field of Search .................. 382/128, 224, 382/227, 228, 155, 156, 225, 133, 134; 364/555, 413.08; 422/73

[56] References Cited

U.S. PATENT DOCUMENTS

| | | | |
|---|---|---|---|
| 4,097,845 | 6/1978 | Bacus | 382/6 |
| 4,661,913 | 4/1987 | Wu et al. | 382/6 |

(List continued on next page.)

FOREIGN PATENT DOCUMENTS

| | | |
|---|---|---|
| 0544385 | 6/1993 | European Pat. Off. . |
| 3-131756 | 6/1991 | Japan . |

OTHER PUBLICATIONS

Kelley et al. "An Adaptive Algorithm For Modifying Hyperellipsoidal Decision Surfaces", 7–11 Jun., 1992 pp. IV–196 to IV–201, IJCNN International Joint Conference on Neural Networks.

Johnson et al. "Multidimensional Self Organisation." 1990 IEEE Int. Workshop on Cellular Neural Networks and Their Appl., Dec. 1990, pp. 254–263.

Gulcur et al. "Identification of Different Types of Leucocytes in Dried Blood Smears Using Neural Networks," Proc. 1992 Int. Biomedical Eng. Days, Aug. 1992, pp. 203–206.

L. Fu et al, "A Hybrid System Approach to Multivariate Analysis of Flow Cytometry Data", Proceedings of the Fifth Annual IEEE Symposium on Computer–Based Medical Systems, ISBN 0–8186–2742–5, Jun. 1992, pp. 315–324.

J. Weber et al., "Guided Data Reduction for Flow Cytometry", Images of the Twenty–First Century, Proceedings of the Annual International Conference of the IEEE Engineering in Medicine and Biology Society, Seattle, WA, USA, vol. 11:1989; pp. 1783–1784.

J. Bezdek et al., "Fuzzy Kohonen Clustering Networks", IEEE International Conference on Fuzzy Systems, Mar. 8–12, 1992, San Diego, CA, USA, pp. 1035–1043.

S. Newton et al., "Adaptive Fuzzy Leader Clustering of Complex Data Sets in Pattern Recognition", IEEE Transactions on Neural Networks, vol. 3, No. 5, Sep. 1992, pp. 794–800.

S–G Kong et al., "Differential Competitive Learning For Phoneme Recognition", Neural Networks For Signal Processing, pp. 1–32.

*Primary Examiner*—Michael T. Razavi
*Assistant Examiner*—Jon Chang
*Attorney, Agent, or Firm*—Banner & Witcoff, Ltd.

[57] ABSTRACT

When a mixture of different kinds of particles, such as blood, is passed through a particle detector such as a flow cytometer to measure various characteristics of each particle and the measurements of two characteristics are plotted on a two-dimensional rectangular co-ordinate, for example, the resultant dots tend to part into groups (clusters) corresponding to the kinds of the particles. This invention relates to a method and a device for presuming informations of the position of center of gravity, variances, number of dots and likes of each cluster by learning and, based upon these informations, presuming a specific cluster or category to which each measured particle should belong from the corresponding measurements of the particle, and it intends to execute such information processing by a fuzzy clustering technique using a neural network.

10 Claims, 4 Drawing Sheets

U.S. PATENT DOCUMENTS

| | | | |
|---|---|---|---|
| 4,791,355 | 12/1988 | Coulter et al. | 324/71.1 |
| 4,965,725 | 10/1990 | Rutenberg | 382/15 |
| 5,255,346 | 10/1993 | Wu et al. | 395/26 |
| 5,555,196 | 9/1996 | Asano | 382/133 |
| 5,555,198 | 9/1996 | Asano | 382/133 |
| 5,627,040 | 5/1997 | Bierre et al. | 382/133 |

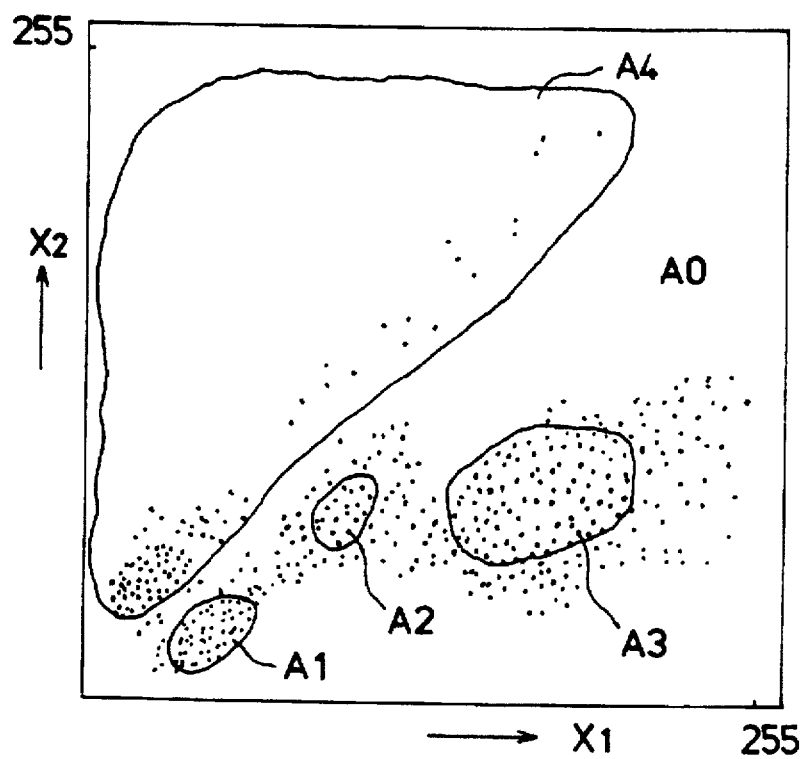
F I G. 7
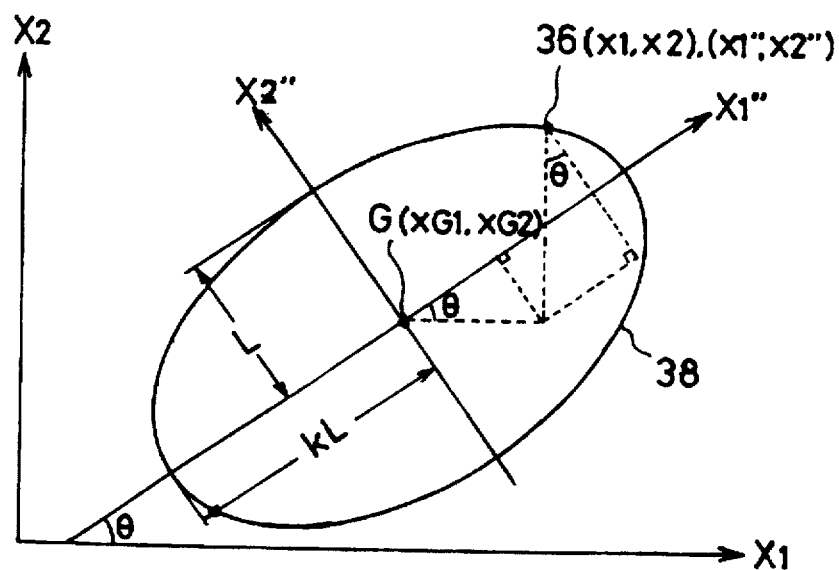
F I G. 8

METHOD AND DEVICE FOR ANALYZING PARTICLES

This application is a continuation of application Ser. No. 08/076,870, filed Jun. 15, 1993, now abandoned.

BACKGROUND OF THE INVENTION

This invention relates to a method and a device for analyzing plural kinds of particles intermixed with each other, by presuming the kind of each particle from measurements of specific characteristics thereof and counting the number of particles belonging to each kind and, especially, to a system for presuming the kind of each particle as detected based upon distribution data obtained by using a neural network and previously applying informations of the respective characteristics of a number of particles thereto to cause it to learn their states of distribution.

While the above-mentioned particle analyzing device is useful, for example, as a blood-corpuscle analyzer for classifying and counting blood-corpuscles in blood, such device is disclosed, for example, in the Japanese opened patent gazette No. H3(91)-131756. In this prior art device, predetermined characteristic values (hereinunder generalized as "characteristic parameters") of blood-corpuscles belonging to plural kinds (hereinunder generalized as "categories") are applied to an input layer of a neural network of error back-propagation type to cause it to learn supervisedly their states of distribution and, thereafter, the characteristic parameters of each particle as detected are supplied to the input layer to cause it to presume the group (hereinunder referred to as "cluster") or the category to which the particle is to belong, that is, to effect a clustering operation, based upon the resultant data of learning.

However, this device has such a disadvantage in that it may erroneously classify a particle of an unlearned category into a learned category when the characteristic parameters of such particle of unlearned category are applied and, moreover, it needs a long time for learning when the distribution of characteristic parameters are complicated, since it uses a neural network of error back-propagation type.

Accordingly, an object of this invention is to provide a method and a device for analyzing particles which can effect an accurate clustering operation within a short time regardless of abnormal or complicated distribution of the characteristic parameters.

SUMMARY OF THE INVENTION

In order to achieve the above-mentioned object, the method and device of this invention are arranged to apply a time-sequence of measured data consisting of plural characteristic parameters to a neural network at the same time as converting them into distribution data in a characteristic parameter space, and presume cluster informations such as center of gravity of the cluster of each category from the distribution data for clustering the detected particle based upon the presumed cluster informations.

More particularly, a mixture of a number of particles belonging to plural categories is supplied to a particle detecting device such as flow cytometer to successively measure predetermined characteristic parameters of each particle and the measured values are converted into distribution data of a predetermined characteristic parameter space. At the same time, the measured values are sequentially supplied to a neural network having an input layer which includes at least neurons respectively corresponding to the above-mentioned characteristic parameters and an output layer which includes at least neurons respectively corresponding to expected categories to execute unsupervised learning vector quantization for presuming cluster informations including center-of-gravity vector informations of the clusters respectively corresponding to the above-mentioned categories and, then, the above-mentioned distribution data are clustered in accordance with the presumed cluster informations.

The presumed cluster informations may include informations of the number and/or variance of the particles in addition to the above-mentioned center-of-gravity vector informations.

These and other features and functions of this invention will be described in more detail below about a preferred embodiment thereof with reference to the accompanying drawings.

BRIEF DESCRIPTION OF THE DRAWINGS

In the drawings:

FIG. 7 is an explanatory diagram of domain division in the operations of FIG. 6;

FIG. 8 is an explanatory diagram of measurement of the distance from a detected particle to the center of gravity of each particle cluster in the operations of FIG. 6;

Thoughout the drawings, same reference numerals are given to corresponding constitutional elements.

DESCRIPTION OF PREFERRED EMBODIMENT

Figure 1:
FIG. 1 is a block diagram showing the configuration of an embodiment of the particle analyzing device according to this invention.
Figure 2A:
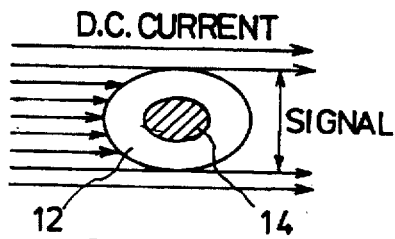
FIGS. 2a and 2b are explanatory diagrams of a blood-corpuscle detecting method in a blood-corpuscle detecting device in the embodiment of FIG. 1.
Figure 2B:
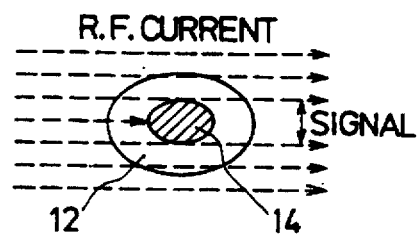

FIG. 1 shows an overall configuration of a blood-corpuscle classifying and counting device as a preferred embodiment of the particle analyzing device of this invention. As shown, the device includes a blood-corpuscle detector 2, a signal amplifier 4, an analog-to-digital (A/D) convertor 6, an analyzing device 8 and a display device 10. The blood-corpuscle detector 2 is a well-known device such as flow cytometer and, when a blood specimen including leukocytes only which are separated by preliminary treatment such as dilution and addition of hemolyzing agent, for example, is supplied thereto, it detects blood-corpuscles one by one and sequentially produces electric signals respectively indicative of predetermined characteristics of the respective blood-corpuscles. For instance, when the blood specimen is passed through a fine passageway which can pass the blood-corpuscles one by one and a d.c. current and a high frequency a.c. current are flowed across the passageway at the same time, the d.c. current results in a signal proportional to the size of the cytoplasm of each blood-corpuscle since the d.c. current is shut out by the cytoplasm 12 as shown in FIG. 2a. in contrast, the high frequency a.c. current penetrates the cytoplasm 12 of low density and low impedance and is shut out by only a nucleus or granule 14 of high density and high impedance as shown in FIG. 2b and, therefore, it results in a signal relating to the density and size of the nucleus or granule. Thus, measured values of two kinds of characteristic parameter are obtained from each blood-corpuscle.

Figure 3:
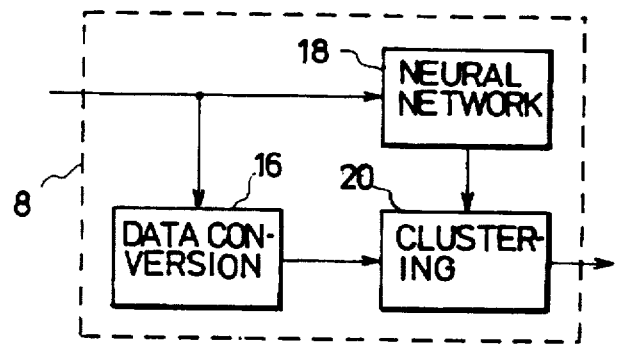
FIG. 3 is a block diagram showing internal configuration of an analyzing device in the embodiment of FIG. 1.

These two kinds of output signal of the blood-corpuscle detector 2 are amplified by the amplifier 4 of well-known type and then converted into digital signals by the A/D convertor 6. In this embodiment, both digital signals are respectively quantized into 256 channels in total from channel No. 0 to No. 255. These two kinds of quantized signals obtained from the respective blood-corpuscles will be hereinunder referred to as data $X(x_1, x_2)$ consisting of a characteristic parameter $x_1$ indicative of the above-mentioned d.c. component and a characteristic parameter $x_2$ indicative of the above-mentioned a.c. component. The data X is then supplied to the analyzing device 8 which is essential to the invention. The analyzing device 8 is composed of a personal computer, microcomputer or microprocessor and functionally includes data processing means 16, a neural network 18 and clustering means 20 as shown in FIG. 3.

Figure 4:
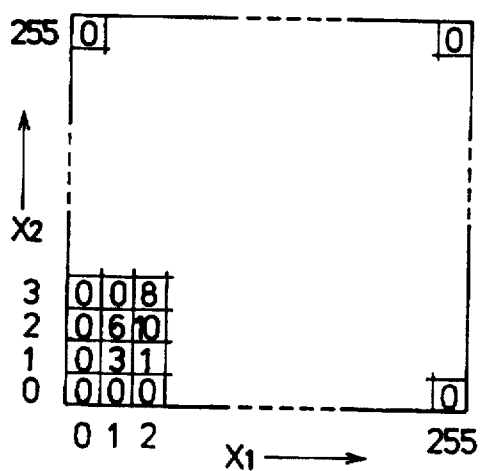
FIG. 4 is a diagram showing an example of distribution data formed by data converting means in FIG. 3.

The data-X are supplied successively to the data converting means 16 and neural network 18. The data X are converted by the data converting means 16 into distribution data $F(x_1, x_2)$ in a two-dimensional space as shown in FIG. 4 having the characteristic parameters $x_1$ and $x_2$ as two variables thereof. Since the characteristic parameters $x_1$ and $x_2$ are quantized respectively into 256 channels as described above, this space of distribution consists of 256×256 basic elements in total, each of which stores the number of blood-corpuscles having their characteristic parameters $x_1$ and $x_2$ belonging to two corresponding channels. For example, FIG. 4 shows that the number of blood-corpuscles whose signal has a d.c. component x1 belonging to channel No. 1 and an a.c. component $x_2$ belonging to channel No. 2 is six and, in other words, F(1, 2)=6. Since the leukocytes include various blood-corpuscles such as lymphocytes, monocytes, granulocytes and the like having different values of the characteristic parameters, the distribution data of FIG. 4 tend to form clusters of the respective kinds of blood-corpuscles. The neural network 18 serves to presume the center of gravity, variances and the number of corpuscles of each cluster based upon the input data X.

Figure 5:
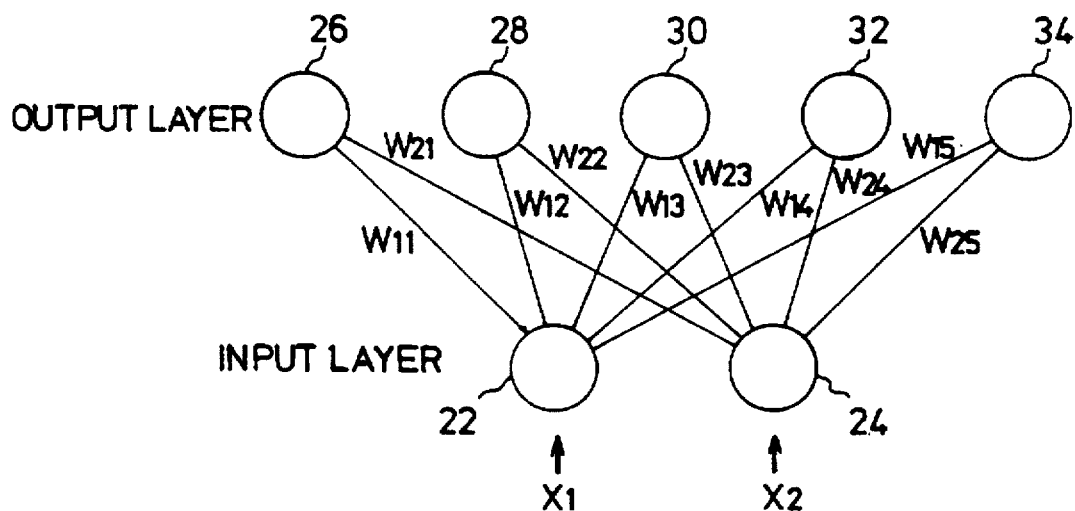
FIG. 5 is an explanatory diagram of an example of the configuration of a neural network in FIG. 3 and a function thereof.

As shown in FIG. 5, the neural network 18 includes an input layer having two neurons 22 and 24 respectively corresponding to the above-mentioned two characteristic parameter inputs $x_1$ and $x_2$ and an output layer having five neurons 26, 28, 30, 32 and 34 respectively corresponding to expected five classification categories, namely, those of lymphocytes, monocytes, granulocytes, ghost corpuscles (unhemolized blood-platelets and erythrocytes) and other corpuscles (immature blood-corpuscles and likes). The neuron 22 in the input layer for the characteristic parameter $x_1$ is connected to the neurons 26, 28, 30, 32 and 34 of the output layer with weights $W_{11}$, $W_{12}$, $W_{13}$, $W_{14}$ and $W_{15}$, respectively, and the input layer neuron 24 for the characteristic parameter $x_2$ is connected to the output layer neurons 26, 28, 30, 32 and 34 with weights $W_{21}$, $W_{22}$, $W_{23}$, $W_{24}$ and $W_{25}$, respectively.

If arbitrary values are initially given to the weights $W_{11}$, $W_{12}$, $W_{13}$, $W_{14}$, $W_{15}$, $W_{21}$, $W_{22}$, $W_{23}$, $W_{24}$ and $W_{25}$ and part or all of the data X to the input layer neurons 22 and 24, the neural network 18 commences a learning operation based upon a method of unsupervised vector quantization. The method of vector quantization is described in detail, for example, in "Neural Networks for Signal Processing", published by Prentice-Hall International Editions.

While the neural network 18 learns a probability density function of the input data X, the above-mentioned weights $W_{11}$ to $W_{15}$ and $W_{21}$ to $W_{25}$ are updated gradually and finally obtained weight vectors $V_1$ (weights $W_{11}$ and $W_{21}$), $V_2$ (weights $W_{12}$ and $W_{22}$), $V_3$ (weights $W_{13}$ and $W_{23}$), $V_4$ (weights $W_{14}$ and $W_{24}$) and $V_5$ (weights $W_{15}$ and $W_{25}$) indicate presumed positions of the centers of gravity of the clusters of lymphocytes, monocytes, granulocytes, ghost corpuscles and other corpuscles in the distribution data $F(x_1, x_2)$, respectively. In the case of normal specimen, the weight vector $V_5$ may be left unchanged from its initial value.

Upon completion of learning, the neural network 18 can presume the number of blood-corpuscles of each kind from relatively few input data since it has learned the probability density function of the input data. More specifically, counters respectively corresponding to the lymphocytes, monocytes, granulocytes, ghost corpuscles and other corpuscles are provided and their counts are assumed as $m_1$, $m_2$, $m_3$, $m_4$ and $m_5$. When a certain datum $X_1$ consists of d.c. and a.c. components $x_{11}$ and $x_{12}$, the values of $(x_{11}-W_{11})^2+(x_{21}-W_{21})^2$, $(x_{11}-W_{12})^2+(x_{21}-W_{22})^2$, $(x_{11}-W_{13})^2+(x_{21}-W_{23})^2$, $(x_{11}-W_{14})^2+(x_{21}-W_{24})^2$ and $(x_{11}-W_{15})^2+(x_{21}-W_{25})^2$ are calculated respectively. In other words, the distances between signal and weight vectors $d_n=\|x_1-W_n\|$ are sought where n=1, . . . 5 and $W_n=(W_{1n}, W_{2n})$. The least one of these distances is selected. For example, when the distance $d_1$ or $(x_{11}-W_{11})^2+(x_{21}-W_{21})^2$ is the least, the count of the corresponding lymphocyte counter is incremented by one. Similar calculations are executed on the other data supplied sequentially thereafter and the least distances are selected to increment the corresponding counters one by one. Then, the finally obtained counts $m_1$ to $m_5$ of the respective counters give the ratio of the presumed numbers of blood-corpuscles belonging to the respective categories, if the respective clusters of the blood-corpuscles are same in distribution. In the case of normal specimen, $m_5$ may be absent and, therefore, the corresponding cluster is not assumed to exist when $m_5$ is less than a predetermined value.

When the numbers of blood-corpuscles are presumed, the data belonging to the respective categories are stored and the variances of the corpuscles in the respective clusters are calculated on the basis thereof. For example, when $X_1(x_{11}, x_{21})$, $X_3(x_{13}, x_{23})$ and $X_7(x_{17}, x_{27})$ are stored as the data belonging to the lymphocyte category, the presumed variance $s_1$ of the lymphocytes is calculated by dividing the sum of total square deviations of $x_{11}$, $x_{13}$ and $x_{17}$ from their mean value and total square deviations of $x_{21}$, $x_{23}$ and $x_{27}$ from their mean value by the number of corpuscles. Presumed variances $s_2$, $s_3$, $s_4$ and $s_5$ of the other categories are similarly obtained. In this case also, $s_5$ need not be calculated if the specimen is normal.

Figure 6:
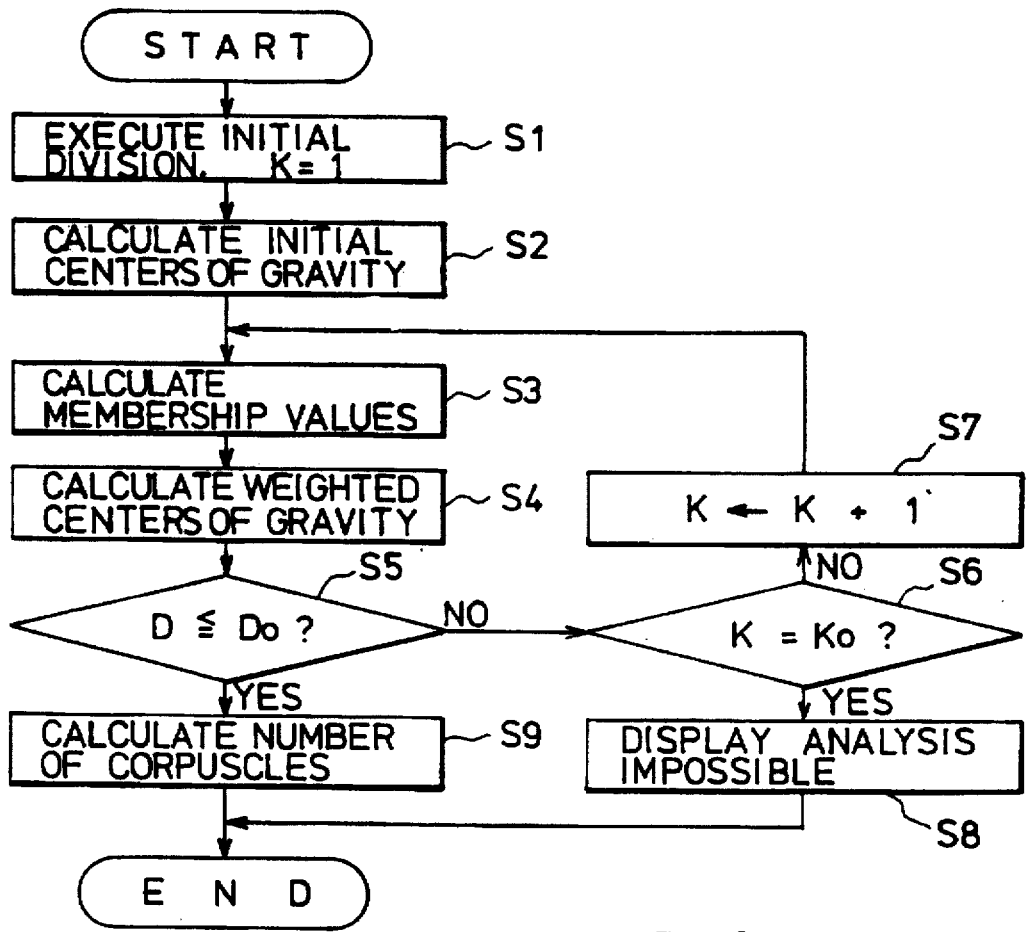
FIG. 6 is a flow chart showing center-of-gravity calculating and particle counting operations in clustering means in FIG. 3.

The blood classifying and counting operation might be completed with the above presumed numbers of corpuscles $m_n$ only if the corpuscles belonging to the respective categories have exhibited the same distribution, the presumed numbers $m_n$ and variances $s_n$ (n=1, ... 5) as obtained above are of approximate values since their distributions are not always same in practice. Therefore, the clustering means 20 clusters the distribution data $F(x_1, x_2)$ obtained from the data converting means 16 by using these approximate values and the presumed centers of gravity $V_n$ (n=1, ... 5) of the respective clusters, which were calculated previously. The operation of the clustering means 20 will be described below with reference to the flow chart of FIG. 6.

Initial division of the distribution data $F(x_1, x_2)$ is carried out first, after a memory value K indicating the number of iterations is set to one (step S1). In this initial division, the distribution of the basic elements in the distribution data of FIG. 4 is divided into four fixed domains $A_1$, $A_2$, $A_3$ and $A_4$ in which the lymphocytes, monocytes, granulocytes and ghost corpuscles are probably distributed respectively, as shown in FIG. 7, regardless of the number of corpuscles stored in each element. In this case, no domain is established for the other corpuscles. Denoting the clusters of lymphocytes, monocytes, granulocytes, ghost corpuscles and other corpuscles with $C_1$, $C_2$, $C_3$, $C_4$ and $C_5$, respectively, the membership values of the blood-corpuscles existing in the above fired domains $A_1$, $A_2$, $A_3$ and $A_4$ to the respective clusters $C_1$, $C_2$, $C_3$ and $C_4$ are assumed as all one (1). The blood-corpuscles belonging to the cluster $C_5$ are undetermined. The domain $A_0$ in FIG. 7 is a domain having undetermined memberships to all clusters $C_1$ to $C_5$.

The initial centers of gravity are determined next (step S2). In this case, assuming the other corpuscles to exist also and using the center-of-gravity vectors presumed by the neural network 18, the initial center-of-gravity positions of the respective clusters $C_1$, $C_2$, $C_3$, $C_4$ and $C_5$ are determined at $(x_{G11}, x_{G21})$, $(x_{G12}, x_{G22})$, $(x_{G13}, x_{G23})$, $(x_{G14}, x_{G24})$ and $(x_{G15}, x_{G25})$, respectively.

Next, membership values of the corpuscles which are not included in any of the fixed domains $A_1$, $A_2$, $A_3$ and $A_4$, that is, the corpuscles distributing in the domain $A_0$ of FIG. 7, to the clusters $C_1$, $C_2$, $C_3$, $C_4$ and $C_5$ are calculated respectively (step S3). To this end, the distance L from each blood-corpuscle in the domain $A_0$ to the center of gravity of each cluster is calculated first. This distance is not an Euclidean distance and it is defined as the minor radius of an ellipse 38 having its center positioned at the center of gravity $(x_{G1n}, x_{G2n})$ and its major axis inclined by an angle $\theta_n$ with respect to the $X_1$-axis of FIG. 7 and passing the corpuscle 36 in question, as shown in FIG. 8 where the suffix n is omitted for simplicity. The angle $\theta_n$ has a value which is previously selected experientially for each cluster $C_n$. The reason why the distance L is so defined is that the actual distributions of all clusters are substantially elliptic in shape. Thus, all corpuscles lying on the same ellipse should be same in distance from the center of gravity and would have the same membership to the cluster $C_n$ as described below.

The distance L can be calculated as follows. If new co-ordinate axes $X_1''$ and $X_2''$ are established along the major and minor axes of the ellipse 38 and the minor and major radii of the ellipse are expressed with L and kL (k is a proportional constant) respectively the point 36 $(x_1'', x_2'')$ on the ellipse is given by the following equation.

$$\left(\frac{x_1''}{kL}\right)^2 + \left(\frac{x_2''}{L}\right) \tag{1}$$

It is solved as follows as looking for the minor radius L.

$$L = \sqrt{x_2''^2 / \left(1 - \frac{x_1''^2}{k^2}\right)} \tag{2}$$

As is understood from FIG. 8, the relation between the co-ordinate $(x_1'', x_2'')$ and the original co-ordinate $(x_1, x_2)$ of the point 36 is given by the following equations.

$$X_1 = \cos\theta_n(x_1 - x_{G1n}) + \sin\theta_n(x_2 - x_{G2n}) \tag{3}$$

$$X_2 = -\sin\theta_n(x_1 - x_{G1n}) + \cos\theta_n(x_2 - x_{G2n}) \tag{4}$$

By applying the equations 3 and 4 to the equation 2 and using the inclination angle $\theta_n$ of each cluster, the distance $L_{n(36)}$ from the blood-corpuscle 36 to the center of gravity of each cluster $C_n$ is calculated. Then, using the presumed number and variance $m_n$ and $s_n$ of the corpuscles in each cluster $C_n$ which are obtained from the neural network 18 as described above the membership $U_{n(36)}$ of the corpuscle 36 to the cluster $C_n$ is given by the following equation.

$$U_{n(36)} = R_{n(36)} / \sum_n R_{n(36)} \tag{5}$$

where $$R_{n(36)} = m_n \sqrt{s_n} / L^2_{n(36)}, (n = 1, 2, \ldots 5) \tag{6}$$

The above equations are based upon such an idea in that the membership is not only inversely proportional to the square distance to the center of gravity of each cluster, but also proportional to the number of corpuscles and the standard deviation of the cluster.

The memberships of each blood-corpuscle in the domain $A_0$ to the respective clusters $C_n$ are calculated as above and each blood-corpuscle is deemed to belong to the respective clusters $C_n$ at rates or weights corresponding to its memberships $U_n$. The positions of the centers of gravity of the respective clusters are corrected taking such weights of each blood-corpuscle with respect-thereto into consideration. In other words, the weighted centers of gravity are calculated (step S4). The co-ordinates $x_{G1n}'$ and $x_{G2n}'$ of the weighted center of gravity of the cluster $C_n$ are given by the following equations.

$$x_{G1n}' = \sum_i \sum_j U_{nij} \cdot N_{ij} \cdot i / \sum_i \sum_j U_{nij} \cdot N_{ij} \tag{7}$$

$$x_{G2n}' = \sum_i \sum_j U_{nij} \cdot N_{ij} \cdot j / \sum_i \sum_j U_{nij} \cdot N_{ij} \tag{8}$$

where i and j are quantized channel numbers of the characteristic parameters $X_1$ and $X_2$ of the distribution data $F(x_1, x_2)$ of FIG. 4 and both of them take such values as 0, 1, 2, ... 255 in this embodiment. $U_{nij}$ is a membership of the basic element belonging to channel Nos. i and j and, $N_{ij}$ is the number of blood-corpuscles in this element.

After calculating the weighted center of gravity of each cluster as above, it is compared with the corresponding initial center of gravity to judge whether the difference D therebetween is equal to or less than a predetermined value $D_0$ or not (step S5). The value of $D_0$ may be zero, for example. If D is not greater than $D_0$ in any cluster, the distances from each blood-corpuscle to respective clusters are not ascertained yet and it is deemed that no membership of this blood-corpuscle to that cluster is decided clearly. In this case, the initial center of gravity of each cluster is updated with the calculated weighted center of gravity and it is judged whether the stored number of iterations K is equal to a predetermined value $K_0$ or not (step S6). If not, the value of K is incremented by one (step S7) and step S3 is resumed for repeating the same operation as updating the center of gravity. If $K=K_0$ is achieved during such repetition, such words as "ANALYSIS IMPOSSIBLE" are displayed by the display device 10 to finish the processing (step S8). On the other hand, if $D \leq D_0$ is achieved in step S5, the memberships of each blood-corpuscle to all clusters have been ascertained and, therefore, the number of the blood-corpuscles in each cluster is calculated based thereupon (step S9). This calculation is executed by either one of two methods as the following.

In the first method, the cluster corresponding to the greatest membership of each blood-corpuscle in the domain $A_0$ is designated as a cluster to which that blood-corpuscle belongs. For example, when a certain basic element contains ten blood-corpuscles and the memberships $U_1$, $U_2$, $U_3$, $U_4$ and $U_5$ of these corpuscles to the clusters $C_1$, $C_2$, $C_3$, $C_4$ and $C_5$ of lymphocytes, monocytes, granulocytes, ghost corpuscles and other corpuscles are 0.95, 0.03, 0.02, 0.00 and 0.00, respectively, all of these ten corpuscles are designated as belonging to the lymphocyte cluster $C_1$. This method is suitable in such a case in that a blood-corpuscle in question exhibits an especially large membership to specific one of the clusters and the clusters are clearly separated. On the other hand, in the second method, the blood-corpuscles in each basic element are shared to the respective clusters at the rate of memberships. Fox example, when the basic element in question contains ten blood-corpuscles and the memberships $U_1$, $U_2$, $U_3$, $U_4$ and $U_5$ of these corpuscles are 0.2, 0.5, 0.3, 0.0 and 0.0, respectively, the memberships other than $U_4$ and $U_5$ are close to each other and it appears that the clusters $C_1$, $C_2$ and $C_3$ are partially overlapping. If all ten corpuscles are shared only to the monocyte cluster of the greatest membership in accordance with the first method in this case, a large counting error may be caused. Therefore, in accordance with proportional distribution based upon the memberships, two, five, three, zero and zero corpuscles are shared respectively to the clusters $C_1$, $C_2$, $C_3$, $C_4$ and $C_5$. This method is effective when the distribution patterns of the respective clusters overlap partially as above. Thus, the clusters to which each blood-corpuscle belongs are decided and the number of corpuscles of each cluster is calculated.

Since in this embodiment, the final center of gravity of each cluster and the major and minor radii of the ellipse representing spread of its distribution are calculated as described above, it is possible to compare these values with their normal values to diagnose their deviation from the normal values, that is, a state of health.

Figure 9A:
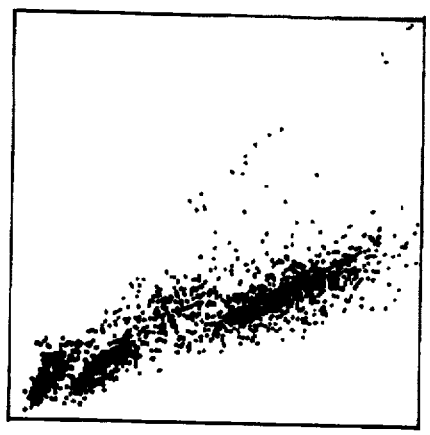
FIGS. 9a and 9b are diagrams showing an example of distribution data of normal blood-corpuscles and a result of clustering thereof.
Figure 9B:
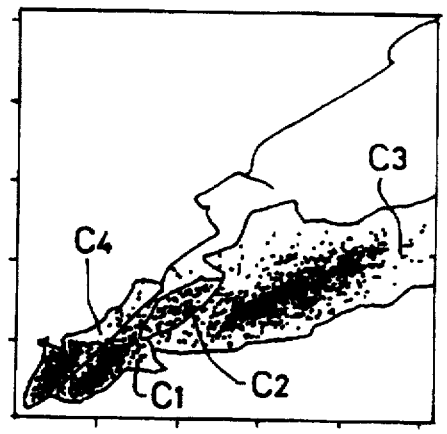
Figure 10A:
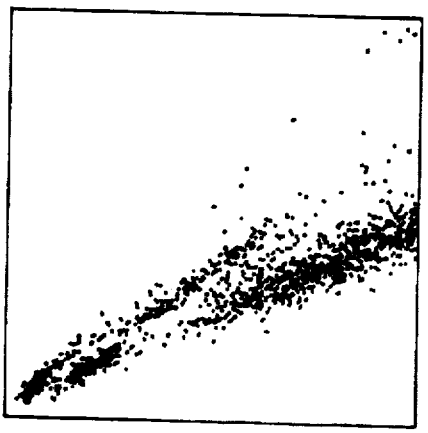
FIGS. 10a and 10b are diagrams showing an example of distribution data of abnormal blood-corpuscles and a result of clustering thereof.
Figure 10B:
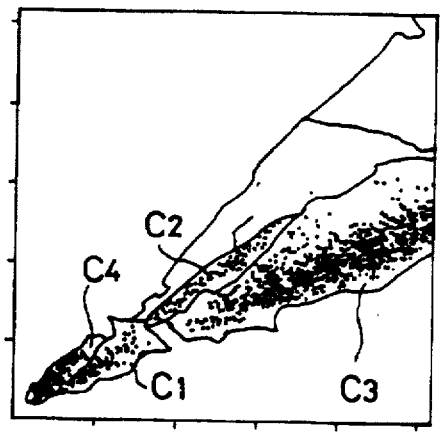
Figure 11A:
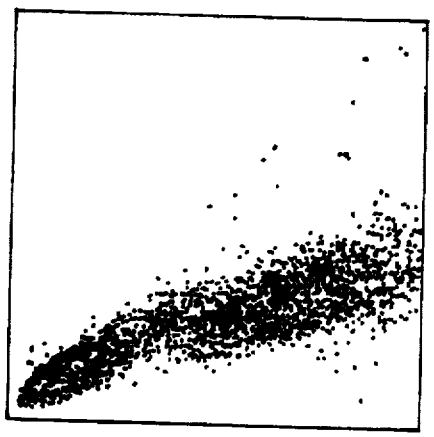
FIGS. 11a and 11b are diagrams showing another example of distribution data of abnormal blood-corpuscles and a results of clustering thereof.
Figure 11B:
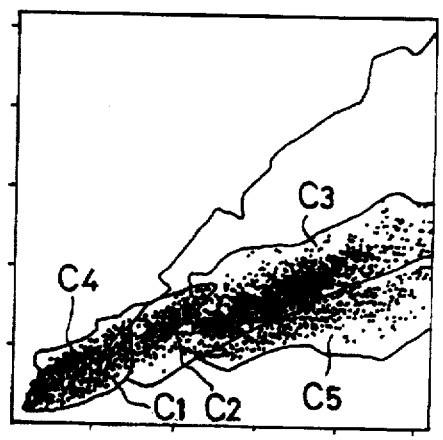

Next, the description will be made about a result of actual execution of this embodiment using a commercially available thirty-two bit personal computer as the analyzing device 8. FIGS. 9a and 9b show scattergrams of a normal specimen and FIGS. 10a, 10b, 11a and 11b show scattergrams of two abnormal specimens. FIGS. 9a, 10a and 11a show their distribution data $F(x_1, x_2)$ before clustering and FIGS. 9b, 10b and 11b show those after clustering. Both normal and abnormal specimens are correctly clustered in this embodiment.

TABLE 1 shows the centers of gravity presumed by the neural network 18 and the centers of gravity finally decided by the succeeding clustering operation, based upon the distribution data $F(x_1, x_2)$ of specimen Nos. 1, 2 and 3 of FIGS. 9a, 10a and 11a. Both are substantially approximate to each other and utility of presumption using the neural network 18 is understood therefrom.

TABLE 2 shows the variances presumed by the neural network 18 and the variances finally decided by the clustering operation, based upon the same distribution data. Although some difference appears therebetween, the presumption has come nearly true.

TABLE 3 shows the numbers of times of operation needed for calculation of the final center of gravity through the clustering operation of the data of the above specimen Nos. 1, 2 and 3, when the presumption by the neural network 18 is used and when it is not used. Although there is no difference between the two in the case of normal specimen No. 1, the neural network shows much less values in the case of abnormal specimen Nos. 2 and 3 and, especially, no good result is obtained without use of the neural network in the case of abnormal specimen No. 3.

TABLE 1

| | (Center of gravity) | | | | | | | | | |
|---|---|---|---|---|---|---|---|---|---|---|
| | Ghost C4 | | Lympho C1 | | Mono C2 | | Granulo C3 | | Others C5 | |
| Specimen | P | F | P | F | P | F | P | F | P | F |
| No.1(Normal) | 22, 25 | 23, 25 | 55, 34 | 54, 31 | 96, 66 | 101, 70 | 165, 79 | 166, 80 | — | — |
| No.2(Abnormal) | 19, 20 | 18, 20 | 56, 36 | 50, 32 | 122, 93 | 128, 95 | 198, 96 | 203, 101 | — | — |
| No.3(Abnormal) | 20, 21 | 20, 21 | 50, 33 | 51, 31 | 92, 63 | 93, 64 | 157, 159 | 159, 79 | 183, 61 | 186, 70 |

(P: Presumed; F: Final)

TABLE 2

| | (Variance) | | | | | | | | | |
|---|---|---|---|---|---|---|---|---|---|---|
| | Ghost C4 | | Lympho C1 | | Mono C2 | | Granulo C3 | | Others C5 | |
| Specimen | P | F | P | F | P | F | P | F | P | F |
| No.1(Normal) | 68 | 66 | 124 | 123 | 432 | 425 | 696 | 693 | — | — |
| No.2(Abnormal) | 38 | 43 | 134 | 127 | 540 | 1029 | 1050 | 1137 | — | — |
| No.3(Abnormal) | 61 | 72 | 183 | 152 | 361 | 3320 | 705 | 788 | 455 | 569 |

(P: Presumed; F: Final)

TABLE 3

| | (Number of operations) | |
|---|---|---|
| Specimen | Presumed | Not presumed |
| No. 1 (Normal) | 2 times | 2 times |
| No. 2 (Abnormal) | 2 times | 4 times |
| No. 3 (Abnormal) | 2 times | 4 times |

The above embodiment is presented for illustrative purpose only and is not intended as any limitation of the invention. It should be obvious to those skilled in the art that various modifications and variations can be made on this embodiment without departing from the spirit and scope of this invention as defined in the appended claims. For example, the particles to be subjected to the inventive analysis need not always be blood-corpuscles, but may be any other kind of particles such as powdered material. In some of such other particles, the above-mentioned distance to the center of gravity may be an Euclidean distance. Moreover, instead of the above-mentioned d.c. and a.c. impedances as the characteristic parameters of the particles, other characteristic signals such as scattered light and fluorescent intensities may be used. Using three or more characteristic parameters, a data distribution in a space of three or higher dimension may be handled. While the center of gravity, the number of particles and the variances of each cluster are used as the object of presumption by the neural network, the center of gravity may be used alone or together with the number of particles. Furthermore, the configuration of the neural network may be modified arbitrarily, which the number of categories is large, for example a suppressive coupling may be inserted between the neurons of the output layer so that, when a specific neuron is excited, the neighboring neurons are suppressed in response thereto.

We claim:

1. In an analyzing device, a method of analyzing a mixture of particles belonging to a plurality of categories to count a number of particles belonging to each of the categories, each particle being individually characterized by a corresponding measured data vector, each measured data vector including a plurality of characteristic parameters, each characteristic parameter being representative of a physical characteristic of a corresponding particle, the method comprising steps of:

converting a plurality of measured data vectors representative of a specimen of particles into a spatial distribution of the plurality of measured data vectors based on spatial dimensions corresponding to the plurality of characteristic parameters, a predetermined number of domains having been predefined in a space of the spatial distribution, the domains including fixed domains and one other domain, each domain defining a respective subspace;

calculating presumed information for each of said plurality of categories from part of the plurality of measured data vectors, the presumed information including a plurality of presumed centers-of-gravity;

determining a corrected center-of-gravity for each category based on the presumed center-of-gravity being used as an initial center-of-gravity, the step of determining a corrected center-of-gravity including initially dividing said particles into said plurality of categories based on the spatial distribution of the measured data vectors and then determining a membership value set for each measured data vector, each membership value set including a membership value corresponding to each domain and being a weight of membership of the measured data vector in the category corresponding to the domain; and clustering said mixture of particles into said plurality of categories based on the spatial distribution of said measured data vectors and based on said corrected center-of-gravity and counting a number of particles belonging to each of the categories of particles based on the membership value sets, wherein the step of determining a membership value set for each measured data vector includes:

when a measured data vector is located in the subspace of said one other domain, calculating the membership value set for each measured data vector based on a distance defined between the measured data vector and the initial center-of-gravity of each category; and when a measured data vector is located in the subspace of a particular domain of the fixed domains, assigning a first value to the membership value corresponding to the particular domain and assigning a second value to the membership value corresponding to another fixed domain different than the particular domain.

2. The method of claim 1, wherein the presumed information includes a presumed count and a presumed variance for each category, and the step of determining a membership value set for each measured data vector further includes assuming the presumed count and the presumed variance to be an initial count and an initial variance for each category, and the step of calculating the membership value set for each measured data vector includes:

calculating a plurality of non-Euclidean distances, each non-Euclidean distance corresponding to a category of the plurality of categories and being defined by a function of a distance between the measured data vector and the initial center-of-gravity of the category; and assigning membership values to the membership value set based on at least one of the non-Euclidean distance, the initial count and the initial variance of the respective category.

3. In an analyzing device, a method of analyzing a mixture of particles belonging to a plurality of categories to count a number of particles belonging to each of the categories, each particle being individually characterized by a corresponding measured data vector, each measured data vector including a plurality of characteristic parameters, each characteristic parameter being representative of a physical characteristic of a corresponding particle, the method comprising steps of:

converting a plurality of measured data vectors representative of a specimen of particles into a spatial distribution of the plurality of measured data vectors based on spatial dimensions corresponding to the plurality of characteristic parameters, a predetermined number of domains having been predefined in a space of the spatial distribution, the domains including fixed domains and one other domain, each domain defining a respective subspace;

calculating presumed information for each of said plurality of categories from part of the plurality of measured data vectors, the presumed information including a plurality of presumed centers-of-gravity;

determining a corrected center-of-gravity for each category based on the presumed center-of-gravity being used as an initial center-of-gravity, the step of determining a corrected center-of-gravity including initially dividing said particles into said plurality of categories based on the spatial distribution of the measured dam vectors and then determining a membership value set for each measured dam vector, each membership value set including a membership value corresponding to each domain and being a weight of membership of the measured data vector in the category corresponding to the domain; and clustering said mixture of particles into said plurality of categories based on the spatial distribution of said measured data vectors and based on said corrected center-of-gravity and counting a number of particles belonging to each of the categories of particles based on the membership value sets, wherein the step of determining a corrected center-of-gravity further includes:

calculating the corrected center-of-gravity for each category based on the membership value sets;

determining a difference between the corrected center-of-gravity and the initial center-of-gravity for each category; and judging that the number of particles belonging to each of the categories of particles is not yet ascertained when the difference determined for any of the categories is greater than a predetermined difference threshold.

4. The method of claim 3, wherein when the number of particles belonging to each of the categories of particles is judged to be not yet ascertained, the step of determining a corrected center-of-gravity further includes steps of:

updating the initial center-of-gravity with the corrected center-of-gravity for each category; and repeating the steps of determining a membership value set for each measured data vector, calculating a corrected center-of-gravity, and determining a difference.

5. The method of claim 4, wherein the step of repeating is successively repeated until an occurrence of an end condition, the end condition being one of:

when a predetermined number of cycles of the step of determining a difference has occurred; and when the difference determined for each category is less than the predetermined difference threshold.

6. An analyzing device for analyzing a mixture of particles belonging to a plurality of categories to count a number of particles belonging to each of the categories, each particle being individually characterized by a corresponding measured data vector, each measured data vector including a plurality of characteristic parameters, each characteristic parameter being representative of a physical characteristic of a corresponding particle, the device comprising:

means for converting a plurality of measured data vectors representative of a specimen of particles into a spatial distribution of the plurality of measured data vectors based on spatial dimensions corresponding to the plurality of characteristic parameters, a predetermined number of domains having been predefined in a space of the spatial distribution, the domains including fixed domains and one other domain, each domain defining a respective subspace;

means for calculating presumed information for each of said plurality of categories from part of the plurality of measured data vectors, the presumed information including a plurality of presumed centers-of-gravity;

means for determining a corrected center-of-gravity for each category based on the presumed center-of-gravity being used as an initial center-of-gravity, the means for determining a corrected center-of-gravity including means for determining a membership value set for each measured data vector, each membership value set including a membership value corresponding to each domain and being a weight of membership of the measured data vector in the category corresponding to the domain; and means for clustering said mixture of particles into said plurality of categories based on the spatial distribution of said measured data vectors and based on said corrected center-of-gravity and for counting a number of particles belonging to each of the categories of particles based on the membership value sets, wherein the means for determining a membership value set for each measured data vector includes:

means, operable when a measured data vector is located in the subspace of said one other domain, for calculating the membership value set for each measured data vector based on a distance defined between the measured data vector and the initial center-of-gravity of each category; and means, operable when the measured data vector is located in the subspace of a particular domain of the fixed domains, for assigning a first value to the membership value corresponding to the particular domain and for assigning a second value to the membership value corresponding to another fixed domain different than the particular domain.

7. The device of claim 6, wherein the information includes a presumed count and a presumed variance for each category, the means for determining a membership value set for each measured data vector includes assuming the presumed count and the presumed variance to be an initial count and an initial variance for each category and the means for calculating the membership value set for each measured data vector includes:

means for calculating a plurality of non-Euclidean distances, each non-Euclidean distance corresponding to a category of the plurality of categories and being defined by a function of a distance between the measured data vector and the initial center-of-gravity of the category; and means for assigning membership values to the membership value set based on at least one of the non-Euclidean distance, the initial count and the initial variance of the respective category.

8. An analyzing device for analyzing a mixture of particles belonging to a plurality of categories to count a number of particles belonging to each of the categories, each particle being individually characterized by a corresponding measured data vector, each measured data vector including a plurality of characteristic parameters, each characteristic parameter being representative of a physical characteristic of a corresponding particle, the device comprising:

means for converting a plurality of measured data vectors representative of a specimen particles into a spatial distribution of the plurality of measured data vectors based on spatial dimensions corresponding to the plurality of characteristic parameters, a predetermined number of domains having been predefined in a space of the spatial distribution, the domains including fixed domains and one other domain, each domain defining a restrictive subspace;

means for calculating presumed information for each of said plurality of categories from part of the plurality of measured data vectors, the presumed information including a plurality of presumed centers-of-gravity;

means for determining a corrected center-of-gravity for each category based on the presumed center-of-gravity being used as an initial center-of-gravity, the means for determining a corrected center-of-gravity including means for determining a membership value set for each measured data vector, each membership value set including a membership value corresponding to each domain and being a weight of membership of the measured data vector in the category corresponding to the domain; and means for clustering said mixture of particles into said plurality of categories based on the spatial distribution of said measured data vectors and based on said corrected center-of-gravity and for counting a number of particles belonging to each of the categories of particles based on the membership value sets, wherein the means for determining a corrected center-of-gravity includes:

means for calculating the corrected center-of-gravity for each category based on the membership value sets;

means for determining a difference between the corrected center-of-gravity and the initial center-of-gravity for each category; and means for judging that the number of particles belonging to each of the categories of particles is not yet ascertained when the difference determined for any of the categories is greater than a predetermined difference threshold.

9. The device of claim 8, wherein the means for determining a corrected center-of-gravity includes means, operable when the number of particles belonging to each of the categories of particles is judged to be not yet ascertained, for updating the initial center-of-gravity with the corrected center-of-gravity for each category, and for repeating an operation of the means for determining a membership value set for each measured data vector, the means for calculating the corrected center-of-gravity, and the means for determining a difference.

10. The device of claim 9, wherein an operation of the means for updating and repealing is successively repeated until an occurrence of an end condition, the end condition being one of:

when a predetermined number of operations of the means for updating and repeating has occurred; and when the difference determined for each category is less than the predetermined difference threshold.

* * * * *